(12) United States Patent
Kim et al.

(10) Patent No.: US 11,345,667 B2
(45) Date of Patent: May 31, 2022

(54) TOTAL SYNTHESIS METHOD OF PACTALACTAM

(71) Applicant: KOREA INSTITUTE OF SCIENCE AND TECHNOLOGY, Seoul (KR)

(72) Inventors: Taejung Kim, Gangneung-si (KR);
Jungyeob Ham, Gangneung-si (KR);
Young Tae Park, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 71 days.

(21) Appl. No.: 16/852,820

(22) Filed: Apr. 20, 2020

(65) Prior Publication Data

US 2020/0331863 A1     Oct. 22, 2020

(30) Foreign Application Priority Data

Apr. 18, 2019   (KR) .................. 10-2019-0045678

(51) Int. Cl.
  *C07D 235/02*     (2006.01)
(52) U.S. Cl.
  CPC .................................. *C07D 235/02* (2013.01)
(58) Field of Classification Search
  CPC .................................................. C07D 235/02
  See application file for complete search history.

(56) References Cited

U.S. PATENT DOCUMENTS

2015/0329570 A1   11/2015   Johnson et al.

OTHER PUBLICATIONS

Kim et al., Org. Lett. 2019, 21,3554-3557, Published May 6, 2019.*
Justin T. Malinowski et al., "Enantioselective Synthesis of Pactamycin, a Complex Antitumor Antibiotic," Science, 2013, pp. 180-182, vol. 340.
Robert J. Sharpe et al., "Asymmetric Synthesis of the Aminocyclitol Pactamycin, a Universal Translocation Inhibitor," Journal of the American Chemical Society, 2013, pp. 17990-17998, vol. 135, American Chemical Society.
Stephen Hanessian et al., "Total Synthesis of Pactamycin and Pactamycate: A Detailed Account," The Journal of Organic Chemistry, 2012, pp. 9458-9472, vol. 77, American Chemical Society.
Stephen Hanessian et al., "Total Synthesis of Pactamycin," Angew. Chem. Int. Ed., 2011, pp. 3497-3500, vol. 50.

\* cited by examiner

*Primary Examiner* — Rebecca L Anderson
(74) *Attorney, Agent, or Firm* — Cantor Colburn LLP

(57) ABSTRACT

The present invention relates to a method of preparing pactalactam represented by Formula 5 below using a total synthesis method:

[Formula 5]

7 Claims, 2 Drawing Sheets

$^1$H NMR spectrum of 2 (500 MHz, MeCN-$d_3$)

$^{13}$C NMR spectrum of 2 (125 MHz, MeCN-$d_3$)

TOTAL SYNTHESIS METHOD OF PACTALACTAM

TECHNICAL FIELD

The present invention relates to a novel method of preparing pactalactam using a total synthesis method.

BACKGROUND ART

Natural products play an important role in medicine. About two-thirds of recently approved drugs are natural products or chemicals inspired by nature.

Natural products are emphasized as essential components of our therapeutics due to abundant biological activity and structural diversity.

Among a very large number of natural bioactive materials, compounds include aminocyclopentitol-containing natural products representing sugar-derived microbial secondary metabolites.

While natural products are relatively rare, they are attractive research subjects because of their biological activity and unique structure.

One of the major members of natural products is soil bacterium *Streptomyces pactum* (*S. pactum*). A large number of pactamycin analogs separated from *S. pactum* and related strains have been reported.

Pactamycin is composed of a steric center, two aromatic rings, and a 5-membered amino cycle site rich in 1,1-dimethylurea. This compound is an aminocyclopentitol-derived natural product having a strong antibacterial effect and a strong anticancer effect.

Since pactamycin has strong cytotoxicity, its use as an anticancer drug is inadequate. Accordingly, it has been necessary to discover novel materials.

According to the present invention, analogs similar to pactamycin could alternatively be approached to extend a range and find characterized nontoxic compounds.

Among the compounds, pactalactam is a natural product reported from *S. pactum* and related strains in a trace amount. The present invention provides a total synthesis method of nontoxic pactalactam.

CITED REFERENCES

Patent Literature (Patent Literature 1) US Patent 2015-0329570

Non-Patent Literatures (Non-Patent Literature 1) *Angew. Chem. Int. Ed.* 2011, 50, 3497-3500.
(Non-Patent Literature 2) *J. Org. Chem.* 2012, 77, 9458-9472.
(Non-Patent Literature 3) *Science* 2013, 340, 180-182.
(Non-Patent Literature 4) *J. Am. Chem. Soc.* 2013, 135, 17990-17998.

DISCLOSURE

Technical Problem

The present invention intends to provide a method of preparing pactalactam, comprising: a first step of preparing a cyclopentenone derivative compound represented by Formula 2 from a phenyloxazoline derivative compound represented by Formula 1; a second step of preparing an N-PMB aziridine (N-para-methoxybenzylamine aziridine) derivative compound represented by Formula 3 from the cyclopentenone derivative compound; a third step of preparing an oxazoline derivative compound containing a cyclopentane core represented by Formula 4 from the N-PMB aziridine derivative compound; and a fourth step of preparing pactalactam represented by Formula 5 from the oxazoline derivative compound containing the cyclopentane core.

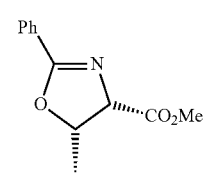

[Formula 1]

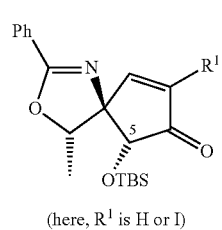

[Formula 2]

(here, $R^1$ is H or I)

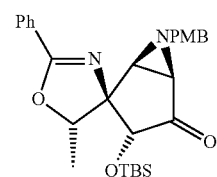

[Formula 3]

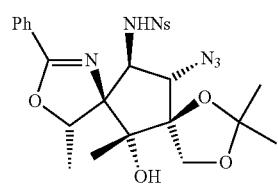

[Formula 4]

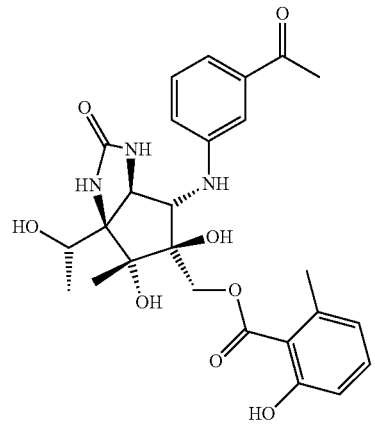

[Formula 5]

Technical Solution

The present invention will be described in detail below. Meanwhile, each description and embodiment disclosed in the present invention may be applied to another description and embodiment. That is, all combinations of the various elements disclosed in the present invention belong to the scope of the present invention. In addition, the scope of the present invention is not to be limited by the specific description described below.

According to an aspect of the present invention, there is provided a method of preparing pactalactam, comprising: a first step of preparing a cyclopentenone derivative compound represented by Formula 2 from a phenyloxazoline derivative compound represented by Formula 1; a second step of preparing an N-PMB aziridine (N-para-methoxybenzylamine aziridine) derivative compound represented by Formula 3 from the cyclopentenone derivative compound; a third step of preparing an oxazoline derivative compound containing a cyclopentane core represented by Formula 4 from the N-PMB aziridine derivative compound; and a fourth step of preparing pactalactam represented by Formula 5 from the oxazoline derivative compound containing the cyclopentane core.

[Formula 1]

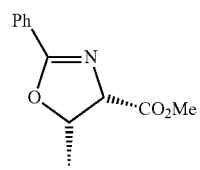

[Formula 2]

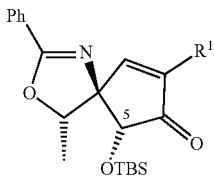

(here, R¹ is H or I)

[Formula 3]

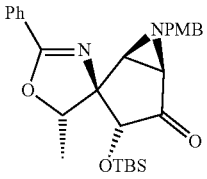

[Formula 4]

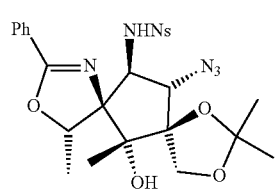

[Formula 5]

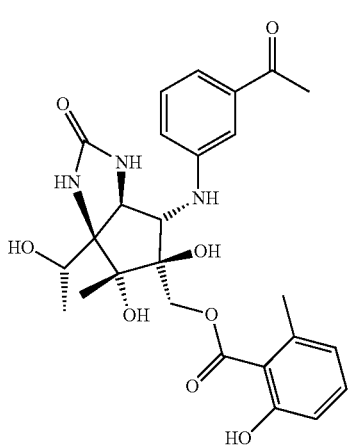

The series of reactions may be carried out in an organic solvent, and the organic solvent may be appropriately selected in consideration of those skilled in the art.

For example, the organic solvent may comprise acetic acid, $CH_3CN$, ethanol, dimethylacetamide (DMA), THF, or $CH_2Cl_2$.

For example, in order to synthesize the pactalactam, the phenyloxazoline derivative compound represented by Formula 1, which is a starting material, may be obtained through inverse synthesis analysis as shown in Reaction Scheme 1 below.

[Reaction Scheme 1]

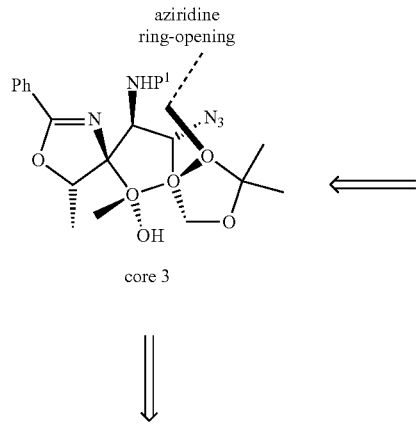

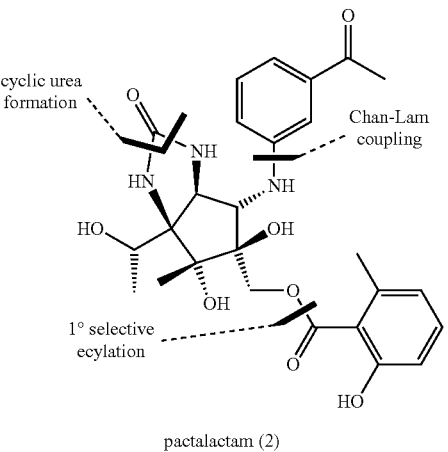

pactalactam (2)

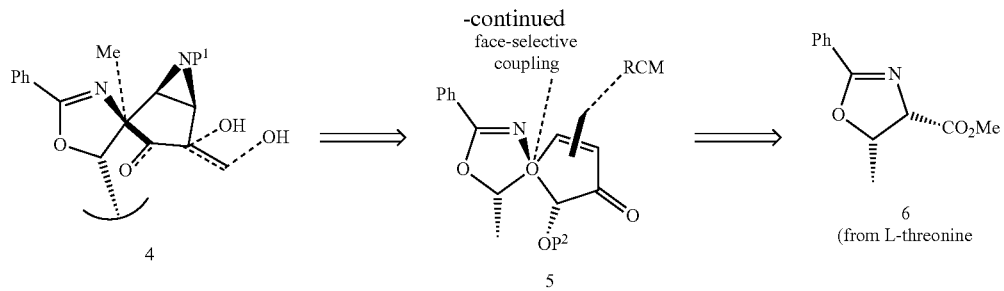

The number 6 in Reaction Scheme 1 above may be referred to as the phenyloxazoline derivative compound of Formula 1.

A cyclopentane core compound 3 is formed from pactalactam through a cyclic urea formation reaction, Chan-Lam coupling, and a 1° selective acylation reaction, the cyclopentane core compound 3 is ring-opened through an aziridine ring-opening reaction to form the compound 4, the compound 4 is formed into the compound 5 through face-selective coupling, and the compound 5 is formed into the compound 6 of Formula 1.

Specifically, the first step may comprise: a first-first step of adding a compound of enolated Formula 1 above using lithium diisopropylamide (LDA) to the compound represented by Formula 1-1 to form a compound represented by Formula 1-2 below; a first-second step of first adding tert-butyldimethylsilyl chloride (TBSCl) to the compound of Formula 1-2 above to react, second diisobutylaluminium hydride (DIBAL-H) to the resulting mixture to react, third adding Dess-Martin periodinane (DMP) to the resulting mixture to react, fourth adding $Ph_3PMeBr$ and n-BuLi to the resulting mixture to react, fifth adding $ZnBr_2$ to the resulting mixture to react, and sixth adding DMP to the resulting mixture to form a compound represented by Formula 1-3 below; a first-third step of first adding vinyl magnesium bromide to the compound of Formula 1-3 above to react, second second-generation Grubbs catalyst to the resulting mixture to form a compound represented by Formula 1-4 below; and a first-fourth step of first adding DMP to the compound of Formula 1-4 above to react, second Iodine ($I_2$) to the resulting mixture to form a compound represented by Formula 2:

[Formula 1-1]

OHC⌒OTr

[Formula 1-2]

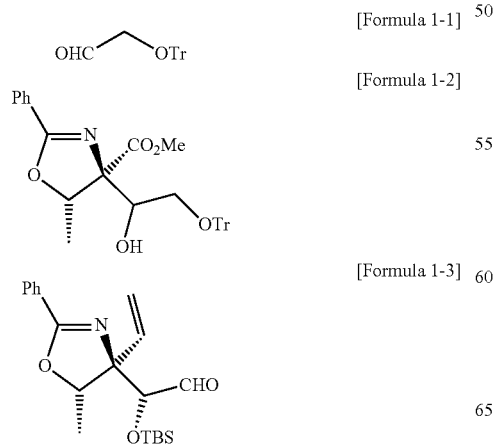

[Formula 1-3]

The compound of Formula 1-2 above may be a mixture of stereoisomers represented by Formula 1-2-a and 1-2-b below, and may be prepared over two steps by adding DMP and $NaBH_4$ to the compound of Formula 1-2-a to convert the compound of Formula 1-2-a into the compound of Formula 1-2-b:

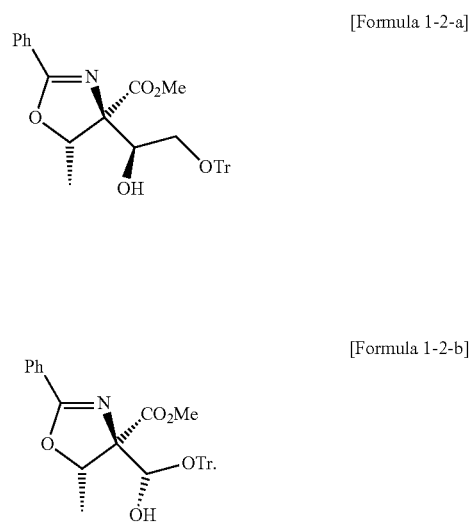

The compound of Formula 1-4 above may be a mixture of stereoisomers represented by Formula 1-4-a and 1-4-b below:

[Formula 1-4-a]

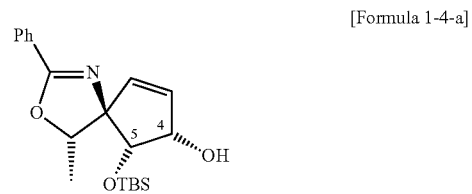

-continued

[Formula 1-4-b]

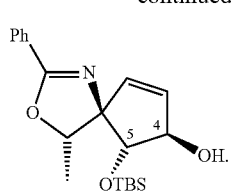

For example, the first step may be represented by Reaction Scheme 2 below.

[Formula 2-1]

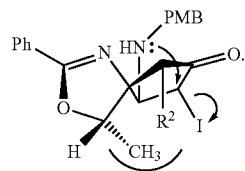

In Formula 2-1 above, $R^2$ may be OTBS (O-tert-Butyldimethylsilyl).

[Reaction Scheme 2]

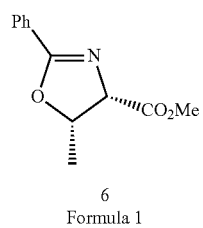

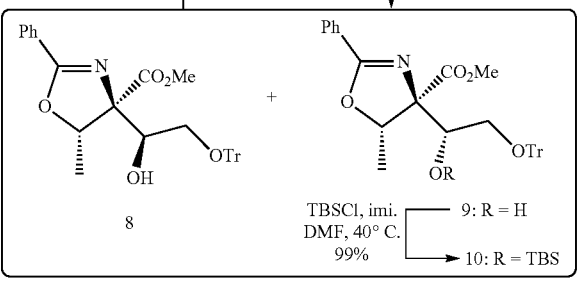

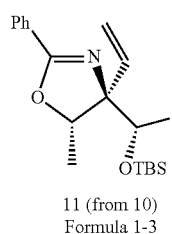

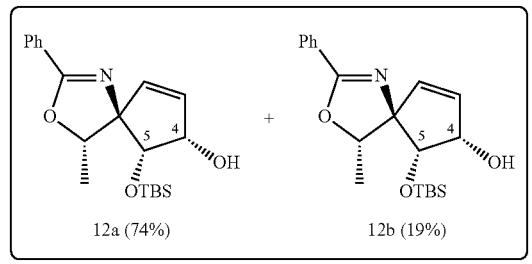

Formula 1-4

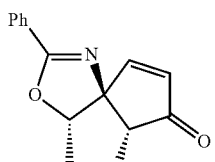

13
Formula 2

Specifically, the second step may include a second-first step of adding $PMBNH_2$ and a compound represented by Formula 2-1 below to the compound of Formula 2 above to form the compound of Formula 3 above.

Specifically, the second step may comprise: a second-first step of adding $I_2$ to the compound of Formula 2 above to form a compound of Formula 2-1 below; a second-second step of adding $PMBNH_2$ to the compound of Formula 2-1 above to form the compound of Formula 3 below.

For example, the second step may be represented by Reaction Scheme 3 below.

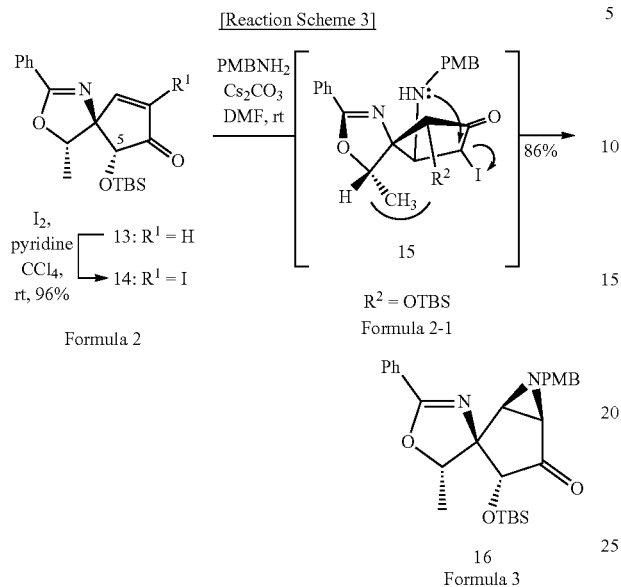

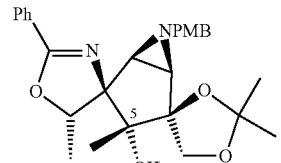

16
Formula 3

Specifically, the third step may comprise: a third-first step of adding MePPh₃Br and n-BuLi to the compound of Formula 3 above to form a compound of Formula 3-1 below; a third-second step of first adding OsO₄ and NMO to the compound of Formula 3-1 above to react, second adding 2,2-dimethoxypropane, and TsOH—H₂O to the resulting mixture to react, third adding tetrabutylammonium bromide (TBAF) to the resulting mixture to react, and fourth adding Dess-Martin periodinane (DMP) to the resulting mixture to form a compound of Formula 3-2 below; a third-third step of adding MeMgBr to the compound of Formula 3-2 above to form a compound of Formula 3-3 below; a third-fourth step of first adding CAN to the compound of Formula 3-3 above to react, second adding NsCl to the resulting mixture to form a compound of Formula 3-4 below; and a third-fifth step of adding NaN₃ to the compound of Formula 3-4 above to form the compound of Formula 4 below.

[Formula 3-1]

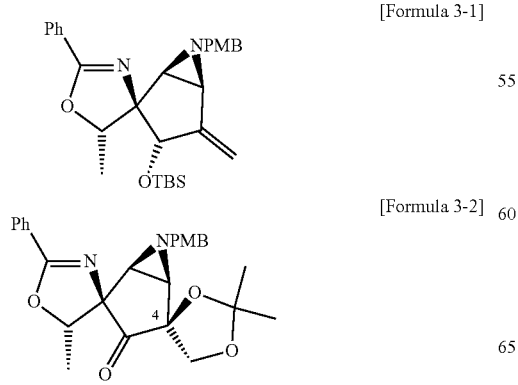

[Formula 3-2]

[Formula 3-3]

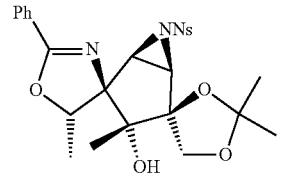

[Formula 3-4]

For example, the third step may be represented by Reaction Scheme 4 below.

[Reaction Scheme 4]

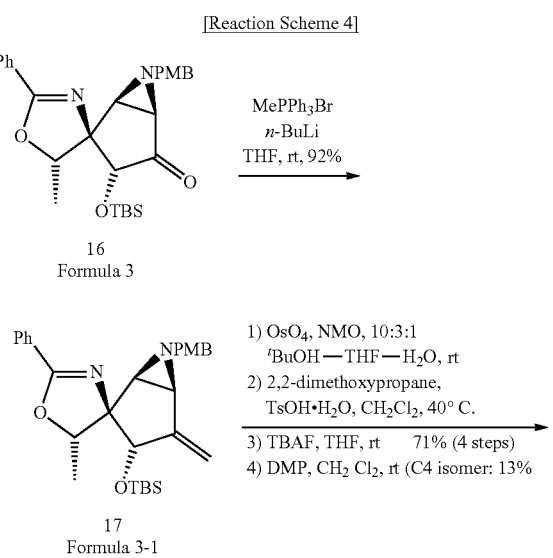

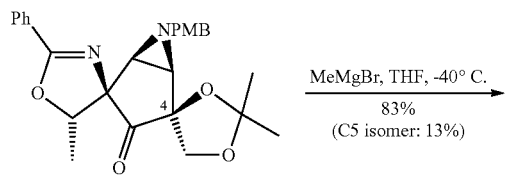

18
Formula 3-2

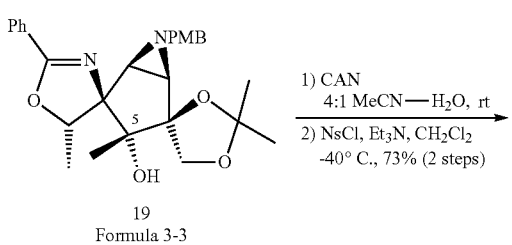

19
Formula 3-3

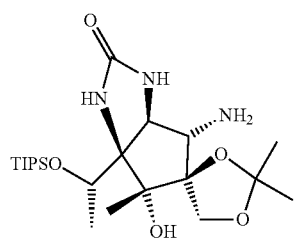

20
Formula 3-4

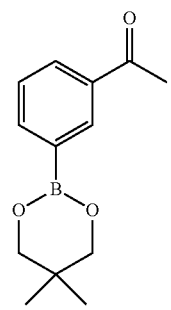

21
Formula 4

Specifically, the fourth step may comprise: a fourth-first step of first adding NaBH₃CN and AcOH to the compound of Formula 4 above to react, and second adding TIPSOTf to the resulting mixture to form a compound of Formula 4-1 below; a fourth-second step of first adding diisopropyl azodicarboxylate (DIAD) to the compound of Formula 4-1 above to react, second adding aqueous HCl solution to the resulting mixture to react, and third adding triphosgene to the resulting mixture to form a compound of Formula 4-2 below; a fourth-third step of first adding 2-mercaptoacetic acid and DBU to the compound of Formula 4-2 above to react, and second adding Zn powder and NH₄Cl to the resulting mixture to form a compound of Formula 4-3 below; a fourth-fourth step of adding a compound represented by Formula 4-4 below, Cu(OAc)₂, DBU, DMAP, and MeCN to the compound of Formula 4-3 above to form a compound of Formula 4-5 below; a fourth-fifth step of first adding tetrabutylammonium bromide (TBAF) to the comp to the compound of Formula 4-5 above to react, and second adding AcOH—H₂O to the resulting mixture to form a compound of Formula 4-6 below; and a fourth-sixth step of adding a compound represented by Formula 4-7 below and K₂CO₃ to the compound of Formula 4-6 above.

[Formula 4-1]

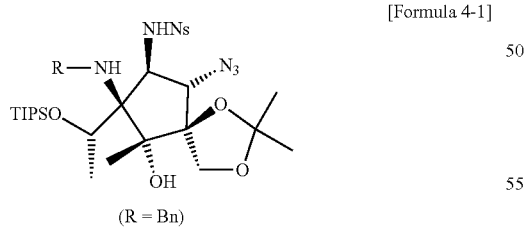

(R = Bn)

[Formula 4-2]

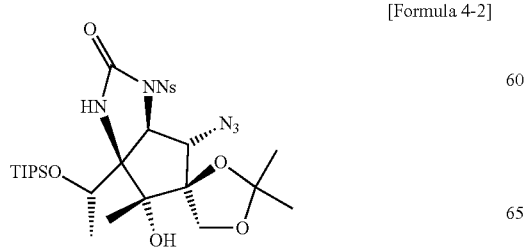

[Formula 4-3]

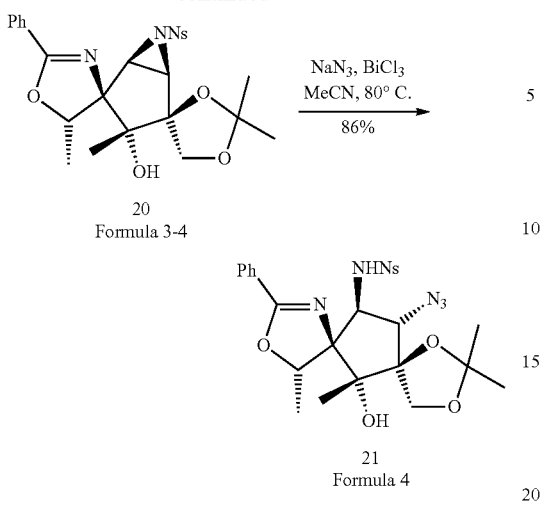

[Formula 4-4]

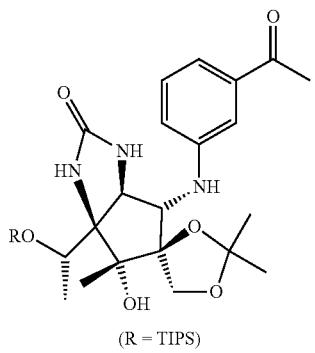

[Formula 4-5]

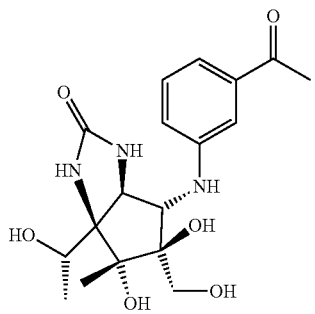

(R = TIPS)

[Formula 4-6]

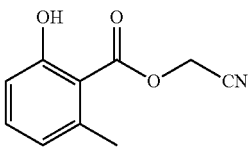

[Formula 4-7]

For example, the fourth step may be represented by Reaction Scheme 5 below.

[Reaction Scheme 5]

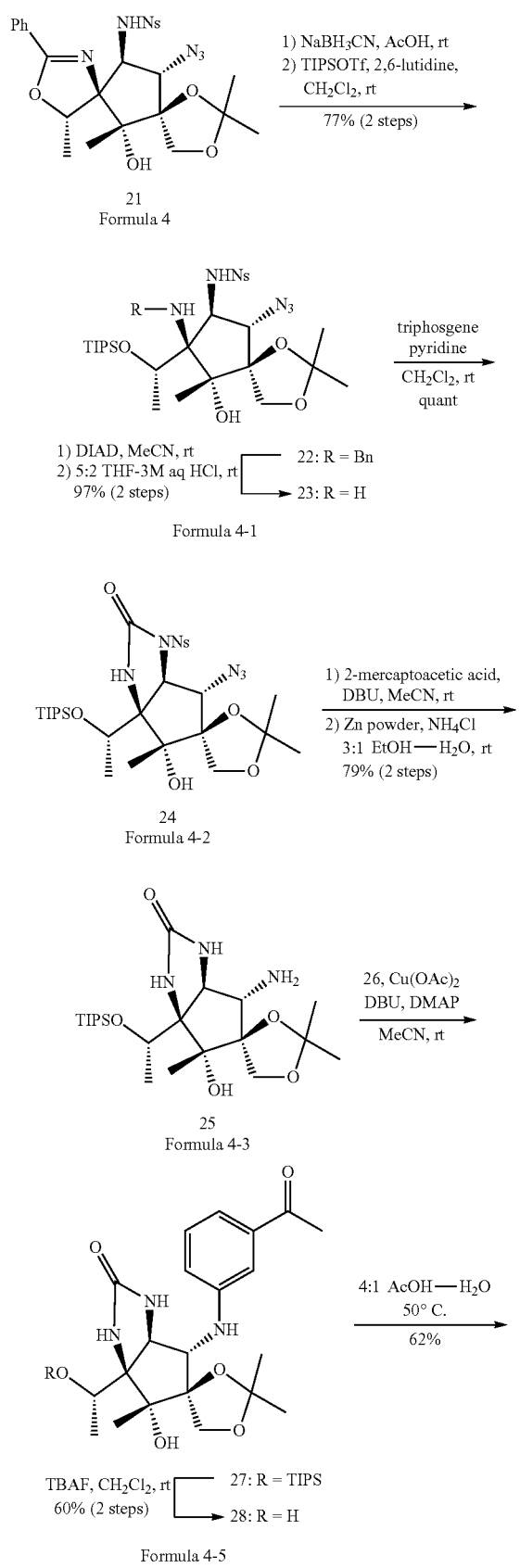

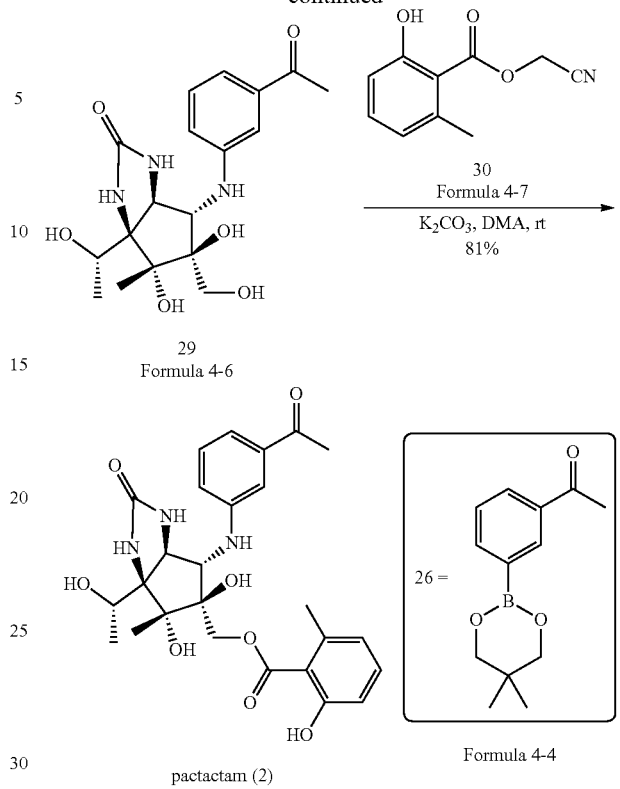

pactactam (2)

As described above, each reaction used in the method of the present invention for preparing pactalactam may be performed under an appropriate organic solvent. The organic solvent may comprise acetic acid, $CH_3CN$, pyridine, water, tert-butanol, DMF, methanol, ethanol, DMA (dimethylacetamide), THF, or $CH_2Cl_2$.

Pactalactam prepared by the method of the present invent for preparing pactalactam resolves the problems caused by the cytotoxicity of conventional pactamycin to provide antiviral, antibacterial, and anticancer effects without cytotoxicity. Further, pactalactam prepared by the method of the present invention for preparing pactalactam may be widely used in new medicines and the like.

Advantageous Effects

The pactalactam of the present invention may provide antiviral, antibacterial, and anticancer effects without cytotoxicity. Further, the pactalactam of the present invention may be widely used in new medicines and the like.

DETAILED DESCRIPTION OF EMBODIMENTS

Figure 1:
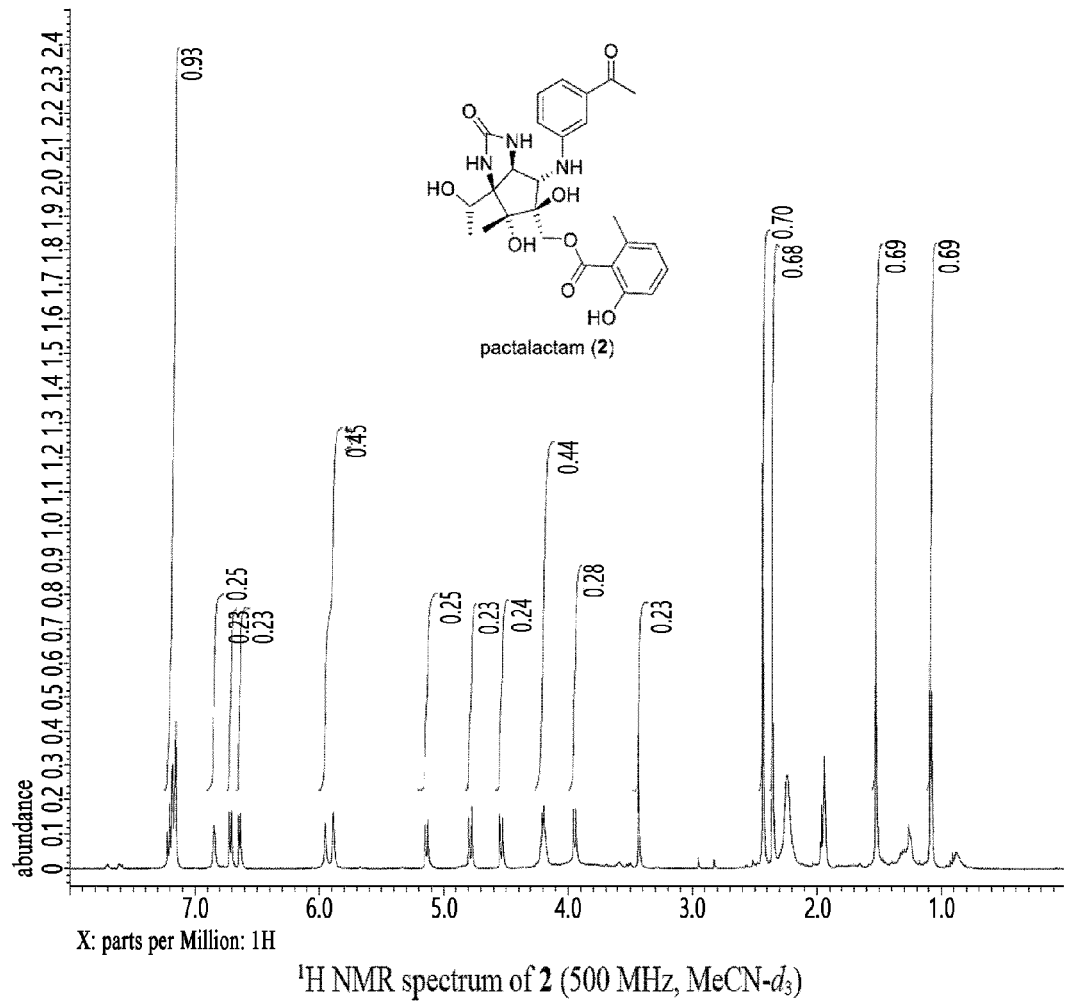
FIG. 1 is a $^1H$ NMR graph of pactalactam obtained by the preparation method according to the present invention.

Hereinafter, the present invention will be described in more detail with reference to embodiments. However, these embodiments are set forth to illustrate the present invention, and the scope of the present invention is not limited to these Examples.

Example 1: Derivation of Starting Material for Preparing Pactalactam

In order to synthesize pactalactam, a phenyloxazoline derivative compound of Formula 1, which is a starting material, was obtained through retrosynthetic Analysis Scheme below.

Retrosynthetic Analysis Scheme:

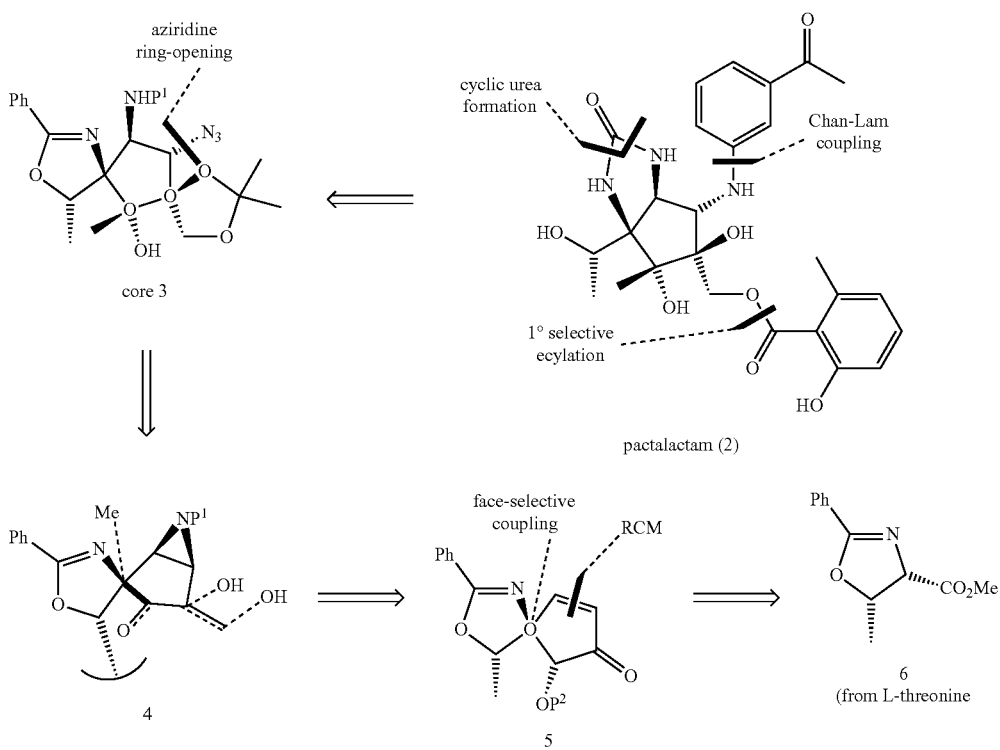

In Retrosynthetic Analysis Scheme, a cyclopentane core compound (core 3 in Reaction Scheme) was formed from pactalactam to be provided in the present invention through a cyclic urea formation reaction, Chan-Lam coupling, and a 1° selective acylation reaction, the core 3 was ring-opened through an aziridine ring-opening reaction, addition of methyl group, dihydroxylation to form the compound of Structural Formula 4, the compound of Structural Formula 4 was formed into the compound of Structural Formula 5 through stereoselective aziridination, and the compound of Structural Formula 5 is formed into the compound of Structural Formula 6, to derive a phenyloxazoline derivative compound, which is a starting material for preparing pactalactam.

Example 2: Method Preparing Pactalactam

A method of preparing pactalactam was performed through first to fourth steps below.

First Step:

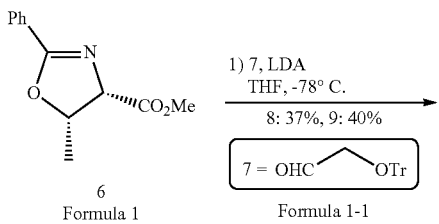

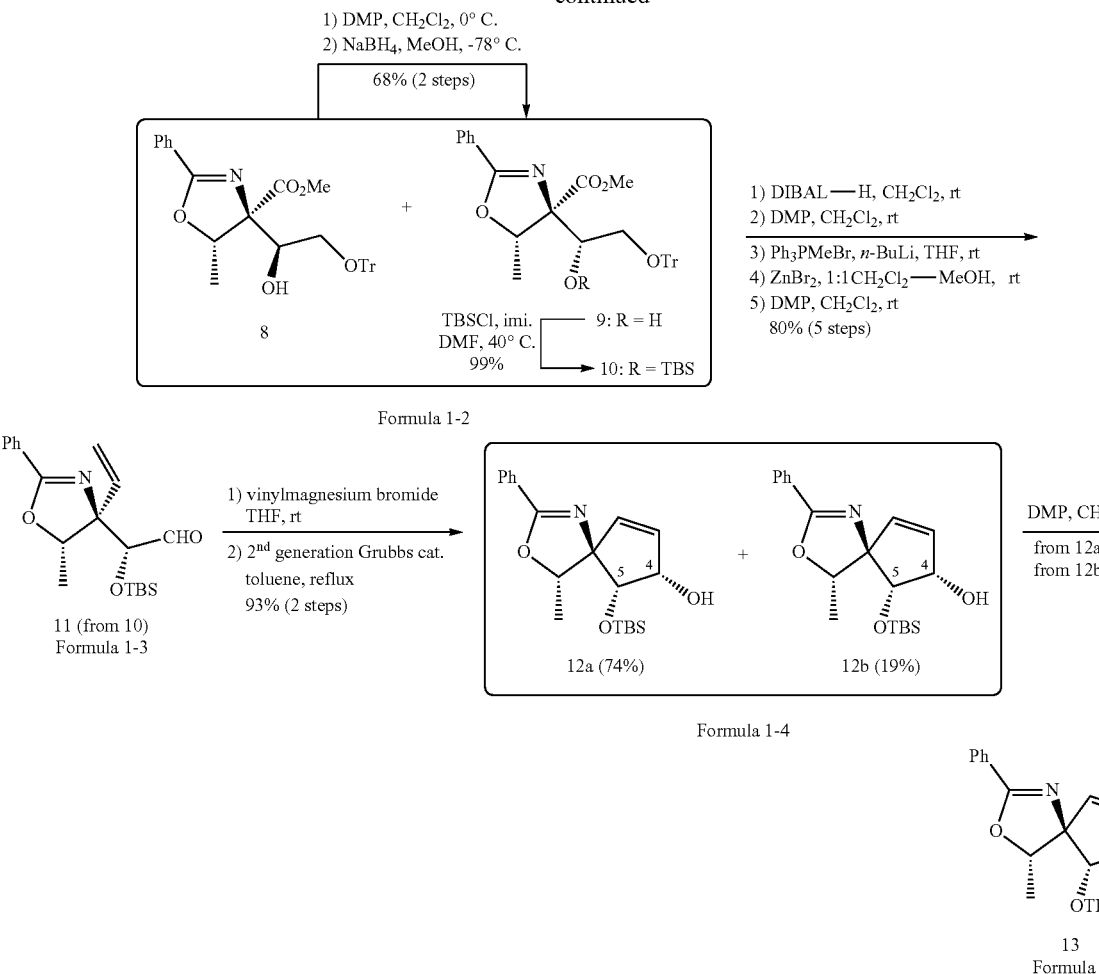

Formula 1-2

Formula 1-3

Formula 1-4

Formula 2

A compound of Formula 1-1 (2.00 g, 6.62 mmol), LDA (lithium diisopropylamide), and THF (tetrahydrofuran, 12 mL) were added to the compound of Formula 1 (1.74 g, 7.94 mmol) through a cannula for 1.5 hours at −78° C. and reacted to form compounds of Formula 1-2, and these compounds of Formula 1-2 were a mixture of stereoisomers. In the compounds of Formula 1-2, DMP (Dess-Martin periodinane, 1.63 g, 3.84 mmol) and $CH_2Cl_2$ (64.0 mL) were added to the compound 8 (1.67 g, 3.20 mmol) at 0° C. and reacted, and $NaBH_4$ and MeOH were added to the compound 8 (1.67 g, 3.20 mmol) at −78° C. and reacted to be formed into the compound 9. In the compound 10 of Formula 1-2, R was converted into H at a yield of 99% when TBSCl (tert-Butyldimethylsilyl chloride, 10.3 g, 95.1 mmol), imi. (imidazole, 10.4 g, 152 mmol), and DMF (N,N-Dimethylformamide, 7.1 mL) were added at 40° C.

In the compound in which R in Formula 1-2 was converted to TBS, compounds were added in five steps to form the compound of Formula 1-3. First, DIBAL-H (diisobutylaluminium hydride, 1.00 M solution in hexane, 20.7 mL, 20.7 mmol) and $CH_2Cl_2$ (68.9 mL) were added to the compound (4.38 g, 6.89 mmol) in which R in Formula 1-2 was converted to TBS and reacted, second, DMP (Dess-Martin periodinane, 3.51 mg, 8.27 mmol) and $CH_2Cl_2$ (138 mL) were added thereto and reacted, third, $Ph_3PMeBr$ (methyltriphenylphosphonium bromide, 6.65 g, 18.6 mmol), n-BuLi (1.65 M THF solution, 10.9 mL, 17.9 mmol), and THF (tetrahydrofuran, 25.0 mL) were added thereto and reacted, fourth, $ZnBr_2$ (15.5 g, 68.9 mmol) and $CH_2Cl_2$ (45.5 mL)-MeOH (8.0 mL) of a ratio of 1:1 were added to the reaction product (4.88 g) obtained from the third reaction and reacted, and fifth, DMP (2.79 g, 6.85 mmol) and $CH_2Cl_2$ (110 mL) were added to the reaction product (1.98 g, 5.48 mmol) obtained from the fourth reaction product to form a compound of Formula 1-3.

After the compound of Formula 1-3 was formed, compounds were added to the compound of Formula 1-3 in two steps to form compounds of Formula 1-4. First, a 1.0 M vinyl magnesium bromide solution and THF (8.20 Ml, 8.20 mmol) were added to a solution in which the compound of Formula 1-3 (1.97 g, 5.48 mmol) is stirred in THF (6.1 mL) and reacted, and second, a second-generation Grubbs catalyst (332 mg, 0.381 mmol) and toluene were added to form a compound 12a (1.45 g, 74%) and compound 12b (384 mg, 19%) of Formula 1-4.

DMP (35.6 mg, 0.0839 mmol) and $CH_2Cl_2$ (1.12 mL) were added to the compound 12a (20.1 mg, 0.0560 mmol) of Formula 1-4 to a compound of Formula 2.

Alternatively, DMP (31.7 mg, 0.0748 mmol) and $CH_2Cl_2$ (1.00 mL) were added to the compound 12b (17.9 mg, 0.0498 mmol) of Formula 1-4 to form a compound of Formula 2.

Second Step:

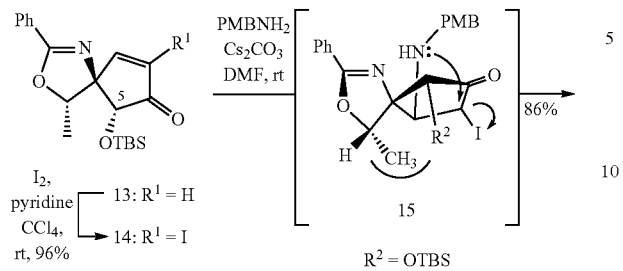

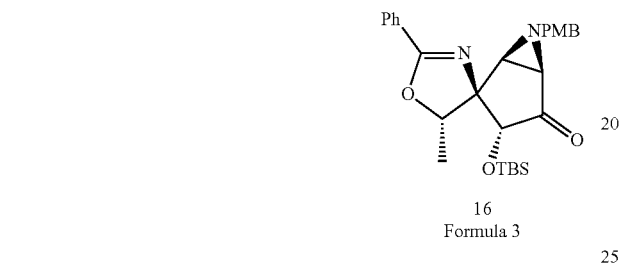

After converting H of $R^1$ in Formula 2 into I by the addition of $I_2$ (4.72 g, 18.6 mmol) and pyridine-$CCl_4$ (62.0 mL), then $PMBNH_2$ (p-methoxybenzylamine, 102 mg, 0.745 mmol), $Cs_2CO_3$ (182 mg, 0.559 mmol), and DMF (N,N-Dimethylformamide, 3.70 mL) were added to a compound of Formula 2-1 in which $R^2$ is OTBS (tert-Butyldimethylsilyl), and a compound of Formula 3 was formed through the intermediate compound of Formula 2-1.

Third Step:

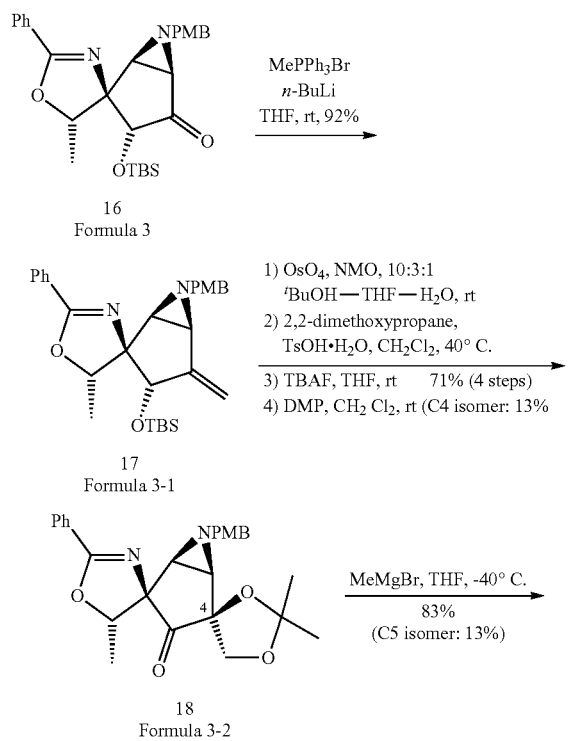

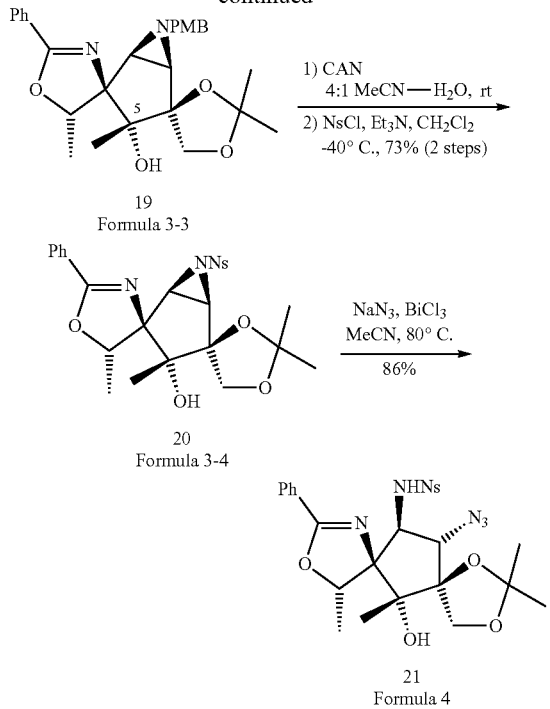

A solution in which $MePPh_3Br$ (methyltriphenylphosphonium bromide, 2.33 g, 6.53 mmol) is stirred, and n-BuLi (1.65 M, THF, 4.11 mL, 6.77 mmol) at 0° C. were added to the compound of Formula 3 (1.19 g, 2.42 mmol) in THF (tetrahydrofuran, 20.2 mL), followed by stirring for 0.5 hours at 0° C.

Compounds were added in four steps to the compound of Formula 3-1 and reacted to form a compound of Formula 3-2.

First, $OsO_4$ (188 mg, 0.741 mmol), NMO (4-methylmorpholine N-oxide, 579 mg, 4.94 mmol) and $^tBuOH$-THF-$H_2O$ (24.7 mL) of a ratio of 10:3:1 were added to the compound of Formula 3-1 (1.21 g, 2.47 mmol) and stirred, second, 2,2-dimethoxypropane, TsOH-$H_2O$ (12.4 mL), and $CH_2Cl_2$ were added and reacted at 40° C., third, TBAF (tetra-n-butylammonium fluoride, 1.0 M solution in THF; 3.71 mL, 3.71 mmol) and THF (24.7 mL) were added, and fourth, DMP (Dess-Martin periodinane, 1.26 g, 2.97 mmol) and $CH_2Cl_2$ (49.4 mL) were added and reacted to form a compound of Formula 3-2.

MeMgBr (3.0 M in THF, 3.95 mL, 11.8 mmol) and THF (47.4 mL) were added to the compound of Formula 3-2 (1.06 g, 2.37 mmol) and reacted at −40° C. to form a compound of Formula 3-3.

Compounds were added to the compound of Formula 3-3 in two steps and reacted to form a compound of Formula 3-4.

First, CAN (ammonium cerium (IV) nitrate, 2.15 g, 3.92 mmol) and MeCN—$H_2O$ (18.0 mL) of a ratio of 4:1 were added to the compound of Formula 3-3 (365 mg, 0.786 mmol) and reacted, and second, NsCl (p-nitrobenzenesulfonyl chloride, 228 mg, 1.03 mmol), $Et_3N$ (0.239 mL, 1.71 mmol), and $CH_2Cl_2$ (17.1 mL) were added and reacted at −40° C. to form a compound of Formula 3-4.

$NaN_3$ (12.4 mg, 0.189 mmol), $BiCl_3$ (17.8 mg, 0.0567 mmol), and MeCN (0.38 mL) were added to the compound of Formula 3-4 (20.0 mg, 0.0378 mmol) and reacted at 80° C. to form a compound of Formula 4.

Fourth Step:

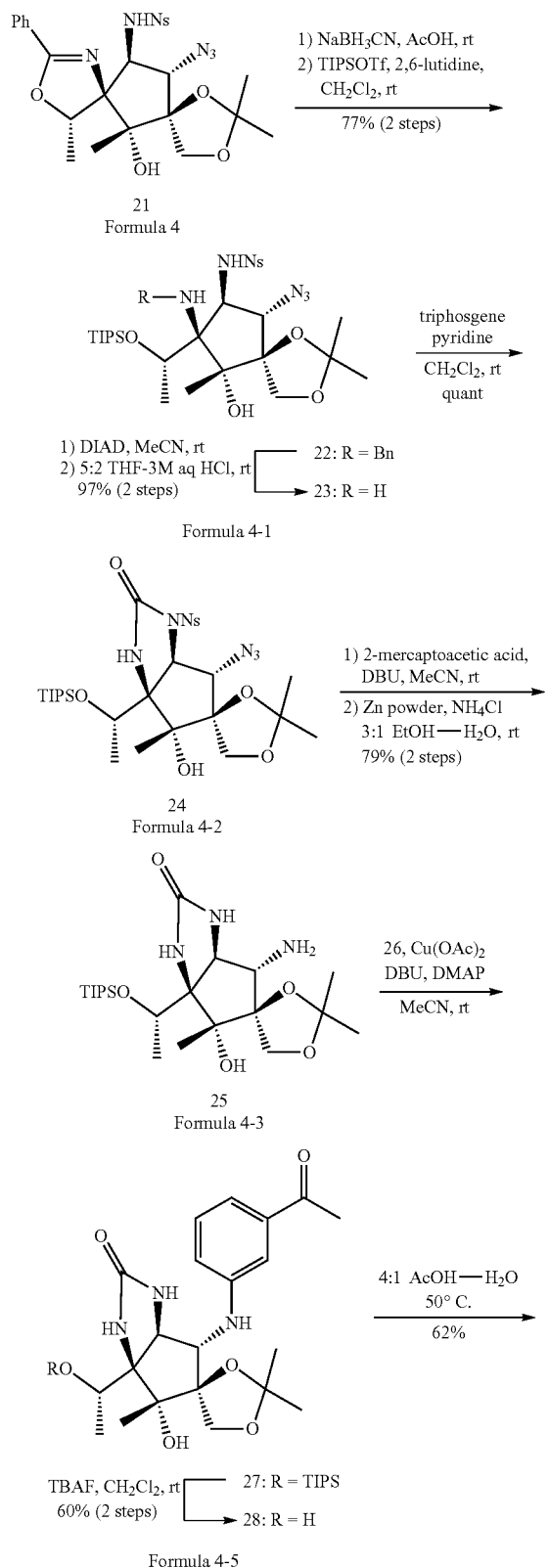

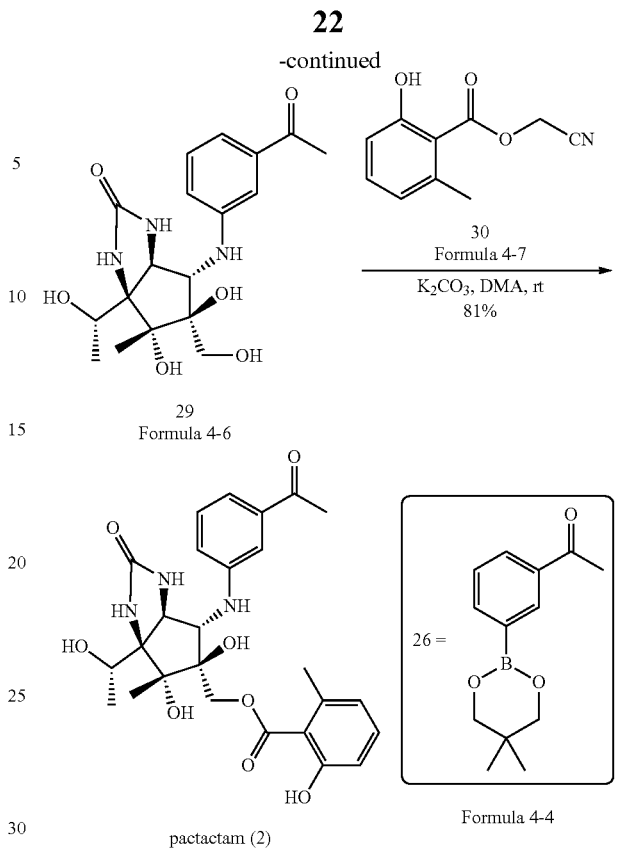

Compounds were added to the compound of Formula 4 in two steps to form a compound of Formula 4-1.

First, NaBH$_3$CN (193 mg, 3.08 mmol) and AcOH (12.8 mL) were added to the compound of Formula 4 (440 mg, 0.770 mmol), and second, TIPSOTf (triisopropylsilyltrifluoromethanesulfonate, 0.198 mL, 0.652 mmol), 2,6-lutidine (0.343 mL, 3.20 mmol), and CH$_2$Cl$_2$ (3.7 mL) were added to form a compound of Formula 4-1.

R of the compound of Formula 4-1 (275 mg, 0.374 mmol) may be converted into H by adding DIAD (diisopropylazodicarboxylate, 0.738 mL, 3.65 mmol) and MeCN (3.7 mL) and then adding THF-3M aqHCl at a ratio of 5:2.

In the compound (112 mg, 0.17 mmol) in which R of Formula 4-1 is converted to H, triphosgene (77.5 mg, 0.26 mmol), pyridine (0.056 mL, 0.711 mmol), and CH$_2$Cl$_2$ (3.5 mL) were added to form a compound of Formula 4-2.

Compounds were added to the compound of Formula 4-2 in two steps to form a compound of Formula 4-3.

First, 2-mercaptoacetic acid (0.035 mL, 0.381 mmol), DBU (1,8-diazabicyclo(5.4.0)undec-7-ene, 0.150 mL, 0.986 mmol), and MeCN (5.0 mL) were added to the compound of Formula 4-2 (168 mg, 0.251 mmol), and second, Zn powder (79.9 mg, 1.22 mmol), NH$_4$Cl (130 mg, 2.44 mmol), and EtOH-H$_2$O (11.1 mL) at a ratio of 3:1 were added to form a compound of Formula 4-3.

A compound of Formula 4-4 (63.4 mg, 0.273 mmol), Cu(OAc)$_2$ (47.2 mg, 0.260 mol), DBU (0.203 mL, 1.36 mmol), DMAP (4-dimethylaminopyridine, 15.9 mg, 0.130 mmol), and MeCN were added to the compound of Formula 4-3 (59.4 mg, 0.130 mmol) to form a compound of Formula 4-5.

R of the compound of Formula 4-5 (50.1 mg, 0.130 mmol) may be converted into H by adding TBAF (tetra-n-butylammonium bromide 0.738 mL, 3.65 mmol) and THF (0.87 mL).

AcOH—H$_2$O (1.12 mmol) at a ratio of 4:1 was added to the compound of Formula 4-5 (23.5 mg, 0.0561 mmol) to form a compound of Formula 4-6.

A compound of Formula 4-7 (29.3 mg, 0.153 mmol), K$_2$CO$_3$ (19.2 mg, 0.139 mmol), and DMA (dimethylacetamide, 0.140 mL) were added to the compound of Formula 4-6 (26.4 mg, 0.0696 mmol) to form pactalactam.

Figure 2:
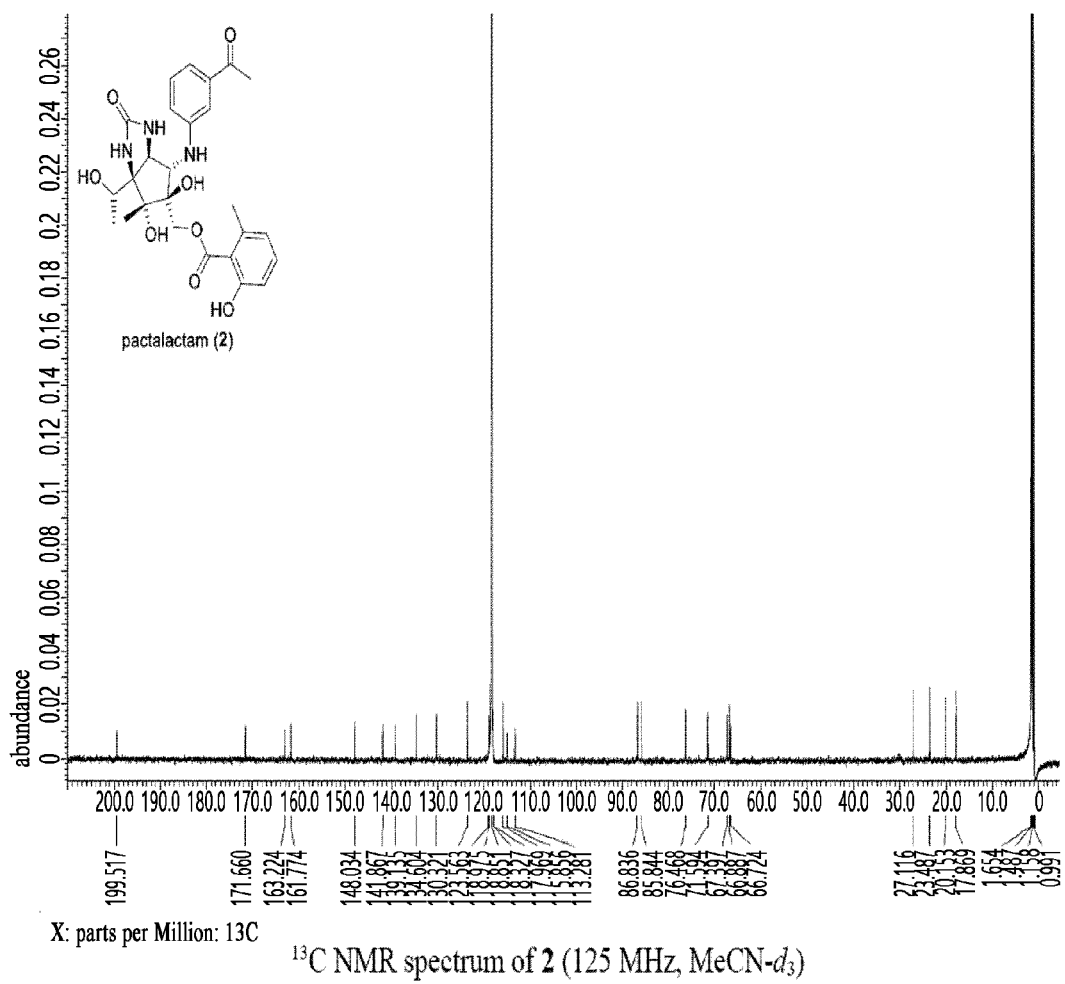
FIG. 2 is a $^{13}C$ NMR graph of pactalactam obtained by the preparation method according to the present invention.

NMR spectrum and $^{13}$C NMR spectrum of the pactalactam of the present invention prepared in the Preparation Example at 400 MHz and at room temperature through Varian MERCURY plus 300, JEOL ECS-400, JEOL ECA-500, or Bruker Avance III were recorded (FIGS. 1 to 2).

Therefore, it was confirmed through NMR analysis that the structural formula of the pactalactam prepared according to the Preparation Example is the same as that of Formula 5, thereby confirming the initial synthesis and structure of pactalactam.

It will be appreciated by those skilled in the art that the present invention as described above may be implemented into other specific forms without departing from the technical spirit thereof or essential characteristics. Thus, it is to be appreciated that embodiments described above are intended to be illustrative in every sense, and not restrictive. The scope of the present invention is represented by the claims to be described below rather than the detailed description, and it is to be interpreted that the meaning and scope of the claims and all the changes or modified forms derived from the equivalents thereof come within the scope of the present invention.

The invention claimed is:

1. A method of preparing pactalactam, the method comprising:
   a first step of preparing a cyclopentenone derivative compound represented by Formula 2 from a phenyloxazoline derivative compound represented by Formula 1;
   a second step of preparing an N-PMB aziridine (N-paramethoxybenzylamine aziridine) derivative compound represented by Formula 3 from the cyclopentenone derivative compound;
   a third step of preparing an oxazoline derivative compound containing a cyclopentane core represented by Formula 4 from the N-PMB aziridine derivative compound; and
   a fourth step of preparing pactalactam represented by Formula 5 from the oxazoline derivative compound containing the cyclopentane core:

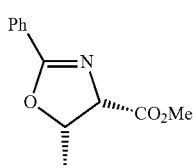

[Formula 1]

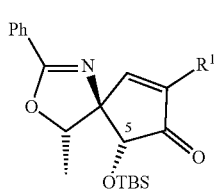

[Formula 2]

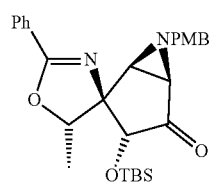

[Formula 3]

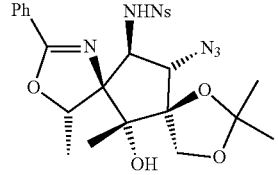

[Formula 4]

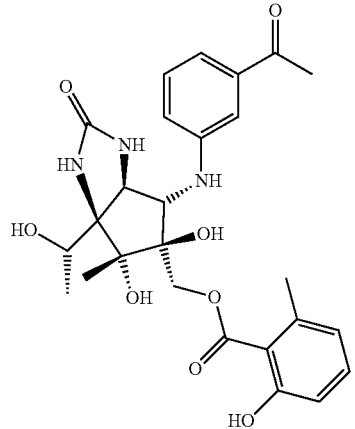

[Formula 5]

wherein, in Formula 2 above, R$^1$ is H or I.

2. The method of claim 1, wherein the first step comprises:
   a first-first step of adding a compound of enolated Formula 1 above using lithium diisopropylamide (LDA) to the compound represented by Formula 1-1 to form a compound represented by Formula 1-2 below;
   a first-second step of first adding tert-butyldimethylsilyl chloride (TBSCl) to the compound of Formula 1-2 above to react, second diisobutylaluminium hydride (DIBAL-H) to the resulting mixture to react, third adding Dess-Martin periodinane (DMP) to the resulting mixture to react, fourth adding Ph$_3$PMeBr and n-BuLi to the resulting mixture to react, fifth adding ZnBr$_2$ to the resulting mixture to react, and sixth adding DMP to the resulting mixture to form a compound represented by Formula 1-3 below;
   a first-third step of first adding vinyl magnesium bromide to the compound of Formula 1-3 above to react, second second-generation Grubbs catalyst to the resulting mixture to form a compound represented by Formula 1-4 below; and
   a first-fourth step of first adding DMP to the compound of Formula 1-4 above to react, second Iodine (I$_2$) to the resulting mixture to form a compound represented by Formula 2:

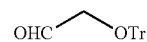

[Formula 1-1]

-continued

[Formula 1-2]

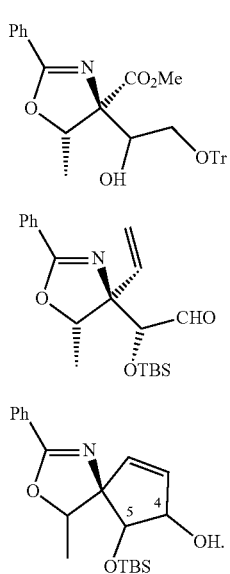

[Formula 1-3]

[Formula 1-4]

3. The method of claim 2, wherein the compound of Formula 1-2 above is a mixture of stereoisomers represented by Formula 1-2-a and 1-2-b below, and the method further comprises a step of adding DMP and NaBH₄ to the compound of Formula 1-2-a to convert the compound of Formula 1-2-a into the compound of Formula 1-2-b:

[Formula 1-2-a]

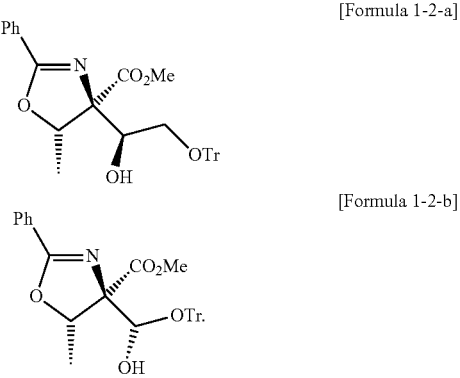

[Formula 1-2-b]

4. The method of claim 1, wherein the second step comprises a second-first step of adding PMBNH₂, and a compound represented by Formula 2-1 below to the compound of Formula 2 above to form the compound of Formula 3 above:

[Formula 2-1]

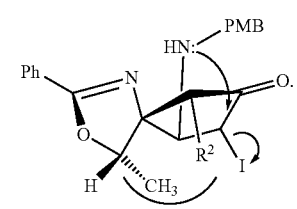

wherein, in Formula 2-1 above, R² is OTBS (O-tert-Butyldimethylsilyl).

5. The method of claim 1, wherein the second step comprises a second-first step of adding I₂ to the compound of Formula 2 above to form a compound of Formula 2-1 below; a second-second step of adding PMBNH₂ to the compound of Formula 2-1 above to form the compound of Formula 3

[Formula 2-1]

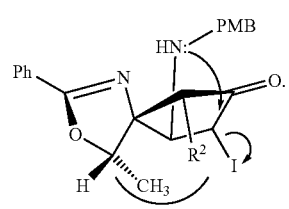

wherein, in Formula 2-1 above, R² is OTBS (O-tert-Butyldimethylsilyl).

6. The method of claim 1, wherein the third step comprises:
a third-first step of adding MePPh₃Br and n-BuLi to the compound of Formula 3 above to form a compound of Formula 3-1 below;
a third-second step of first adding OsO₄ and NMO to the compound of Formula 3-1 above to react, second adding 2,2-dimethoxypropane, and TsOH-H₂O to the resulting mixture to react, third adding tetrabutylammonium bromide (TBAF) to the resulting mixture to react, and fourth adding Dess-Martin periodinane (DMP) to the resulting mixture to form a compound of Formula 3-2 below;
a third-third step of adding MeMgBr to the compound of Formula 3-2 above to form a compound of Formula 3-3 below;
a third-fourth step of first adding CAN to the compound of Formula 3-3 above to react, second adding NsCl to the resulting mixture to form a compound of Formula 3-4 below; and
a third-fifth step of adding NaN₃ to the compound of Formula 3-4 above to form the compound of Formula 4:

[Formula 3-1]

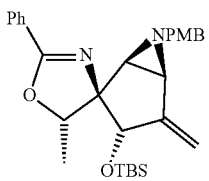

[Formula 3-2]

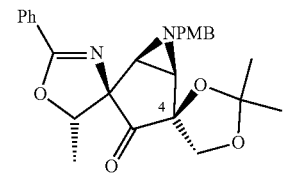

[Formula 3-3]

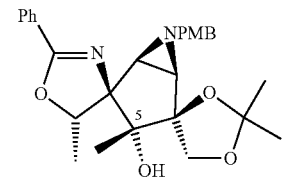

[Formula 3-4]

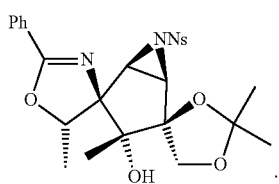

7. The method of claim 1, wherein the fourth step comprises:
- a fourth-first step of first adding NaBH₃CN and AcOH to the compound of Formula 4 above to react, and second adding TIPSOTf to the resulting mixture to form a compound of Formula 4-1 below;
- a fourth-second step of first adding diisopropyl azodicarboxylate (DIAD) to the compound of Formula 4-1 above to react, second adding aqueous HCl solution to the resulting mixture to react, and third adding triphosgene to the resulting mixture to form a compound of Formula 4-2 below;
- a fourth-third step of first adding 2-mercaptoacetic acid and DBU to the compound of Formula 4-2 above to react, and second adding Zn powder and NH₄Cl to the resulting mixture to form a compound of Formula 4-3 below;
- a fourth-fourth step of adding a compound represented by Formula 4-4 below, Cu(OAc)₂, DBU, DMAP, and MeCN to the compound of Formula 4-3 above to form a compound of Formula 4-5 below;
- a fourth-fifth step of first adding tetrabutylammonium bromide (TBAF) to the comp to the compound of Formula 4-5 above to react, and second adding AcOH—H₂O to the resulting mixture to form a compound of Formula 4-6 below; and
- a fourth-sixth step of adding a compound represented by Formula 4-7 below and K₂CO₃ to the compound of Formula 4-6:

[Formula 4-1]

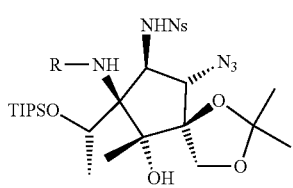

[Formula 4-2]

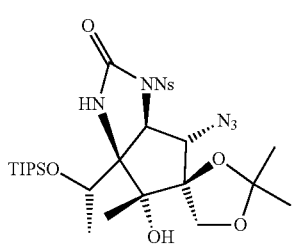

[Formula 4-3]

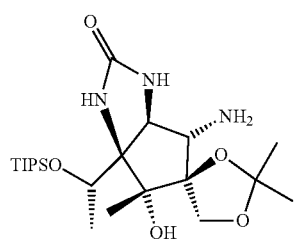

[Formula 4-4]

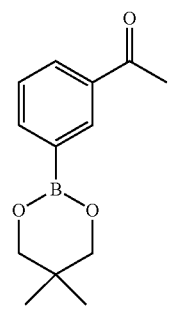

[Formula 4-5]

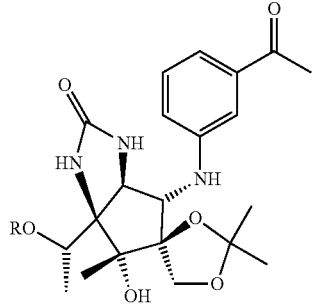

[Formula 4-6]

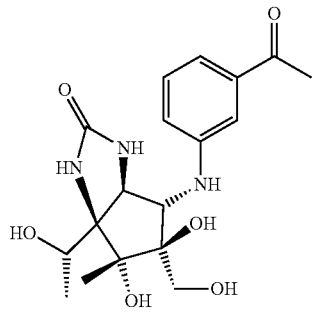

[Formula 4-7]

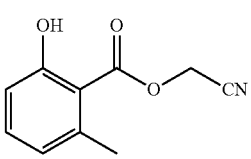

wherein, in Formula 4-1 above, R is Bn or H; and in Formula 4-5 above R is TIPS (triisopropylsilyl) or H.

* * * * *